United States Patent
Caufield et al.

[11] Patent Number: 5,151,413
[45] Date of Patent: Sep. 29, 1992

[54] RAPAMYCIN ACETALS AS IMMUNOSUPPRESSANT AND ANTIFUNGAL AGENTS

[75] Inventors: Craig E. Caufield, Plainsboro, N.J.; Guy A. Schiehser, Yardley, Pa.

[73] Assignee: American Home Products Corporation, New York, N.Y.

[21] Appl. No.: 788,682

[22] Filed: Nov. 6, 1991

[51] Int. Cl.$^5$ .................. A61K 31/695; A61K 31/395; C07D 498/16; C07D 7/04

[52] U.S. Cl. ...................................... 514/63; 514/291; 540/452; 540/456

[58] Field of Search ............... 540/456, 452; 514/291, 514/63

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal | 424/122 |
| 4,316,885 | 2/1982 | Rakhit | 424/122 |
| 4,401,653 | 4/1983 | Eng | 424/122 |
| 4,650,803 | 3/1987 | Stella | 314/291 |
| 4,885,171 | 12/1989 | Sehgal | 424/122 |

OTHER PUBLICATIONS

J. Antibiot. 28, 721–726 (1975).
J. Antibiot. 28, 727–732 (1975).
J. Antibiot. 31, 539–545 (1978).
Can. J. Phsiol. Pharmacol. 55, 48 (1977).
FASEB 3, 3411 (1989).
FASEB 3, 5256 (1989).
Lancet, 1183, (1978).

*Primary Examiner*—Robert T. Bond
*Attorney, Agent, or Firm*—Robert F. Boswell, Jr.

[57] ABSTRACT

Derivatives of Rapamycin where the hydroxy group at position 31 and/or 42 are reacted with acetal forming reagents have been shown to have immunosuppressant and antifungal properties. These derivatives are represented by the formula:

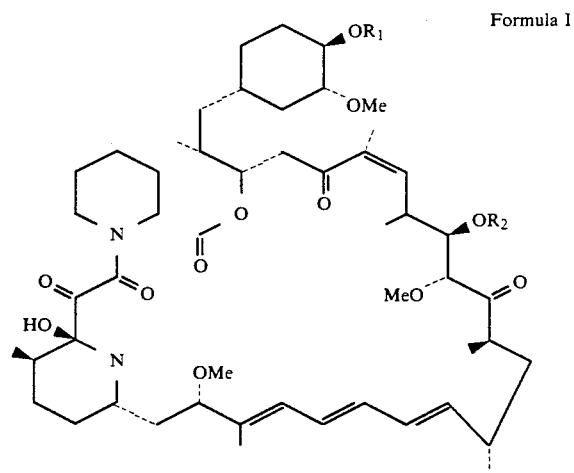

Formula I wherein $R^1$ and $R^2$ independently are hydrogen, $-CH_2YX$, $-C(CH_3)_2YX$, $-CH_2(CH_3)YX$, or L; Y is O or S; X is $-CH_3$, $-(CH_2)_nCH_3$, $-CH_2C_6H_6$, $-(CH_2)_2OCH_3$, $-CH_2Cl_3$ or $-CH_2CH_2Si(CH_3)_3$ and L is selected from tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-S, S-dioxide-2-yl with a proviso that $R^1$ and $R^2$ cannot simultaneously be hydrogen and n is 1–5.

13 Claims, No Drawings

RAPAMYCIN ACETALS AS IMMUNOSUPPRESSANT AND ANTIFUNGAL AGENTS

BACKGROUND OF THE INVENTION

This invention relates to acetals of rapamycin, their immunosuppressant properties and their antifungal activity. This invention further relates to pharmaceutical compositions containing rapamycin acetals.

Rapamycin is a macrolide antibiotic produced by *Streptomyces hydroscopicus* having profound antifungal activity, especially against *Candida albicans*, and low toxicity [U.S. Pat. Nos. 3,929,992 and 3,993,749; Journal of Antibiotics 28(10), 721–726, 727–732 (1975) and journal of Antibiotics 31(6), 539–545 (1978)].

Rapamycin was reported to inhibit the immune response in Can. J. Physiol. Pharmacol. 55, 48–51 (1977). U.S. Pat. No. 4,316,885 discloses monoacyl and diacyl derivatives of rapamycin, especially the acetylated derivatives which are useful antifungal antibiotics. A. U.S. Pat. application Ser. No. 957,626 filed Nov. 3, 1978 which ultimately resulted in U.S. Pat. No. 4,885,171 discloses a method for treating carcinogenic tumors in mammals with rapamycin. U.S. Pat. No. 4,401,653 discloses a method of using rapamycin and picibanil in combination for the treatment of transplantable carcinogenic tumors. U.S. Pat. No. 4,650,803 discloses aminoalkylcarboxylic acid esters of rapamycin at positions 31 and/or 42 which are water soluble prodrug forms of rapamycin.

SUMMARY OF THE INVENTION

The present invention is concerned with acetals of rapamycin of Formula I or pharmaceutically acceptable salts thereof, which possess immunosuppressive and/or antifungal and/or antitumor and/or antiinflammatory activity in vivo and/or inhibit thymocyte proliferation in vitro and are therefore useful in the treatment of transplantation rejection, autoimmune diseases (i.e., lupus, rheumatoid arthritis, diabetes mellitus, multiple sclerosis), *Candida albicans* injections, and diseases of inflammation.

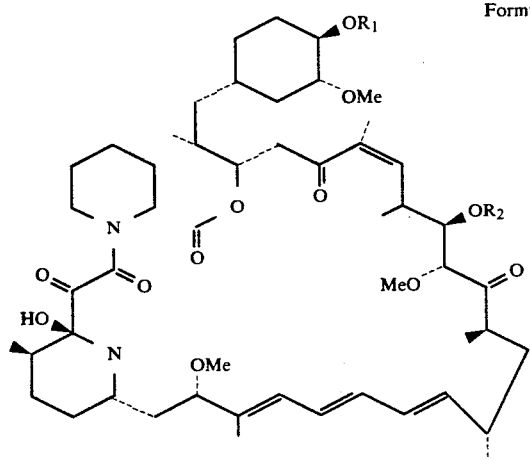

Formula I

Under Formula I, $R^1$ and $R^2$ are independently hydrogen, $-CH_2YX$, $-C(CH_3)_2YX$, $-CH(CH_3)YX$, or L; where Y is O or S;

X is $-CH_3$, $-(CH_2)_nCH_3$, $-CH_2Ar$, $-(CH_2)_2OCH_3$, $-CH_2CCl_3$, $-CH(CH_3)_2$ or $-CH_2CH_2SiMe_3$;

L is tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-2-yl S,S-dioxide; and where n=1–5, with proviso that $R^1$ and $R^2$ cannot both be hydrogen simultaneously.

DETAILED DESCRIPTION OF THE INVENTION

The Formula I compounds are prepared by reacting rapamycin with acetal forming reagents using standard literature procedures. The acetal forming reagents are those employed in protecting secondary hydroxyl groups and are described in Theodora Green, *Protective Groups in Organic Synthesis* (John Wiley and Sons, Inc., 1981), pp 16–26. These reactions consist of reacting rapamycin with various halomethylethers or thioethers in the presence of a base, for example, sodium hydride, triethylamine, or ethyl diisopropylamine; or reacting rapamycin with a vinyl ether under acidic conditions to obtain the acetals of the instant invention as shown in the reaction schemes 1 and 2 below.

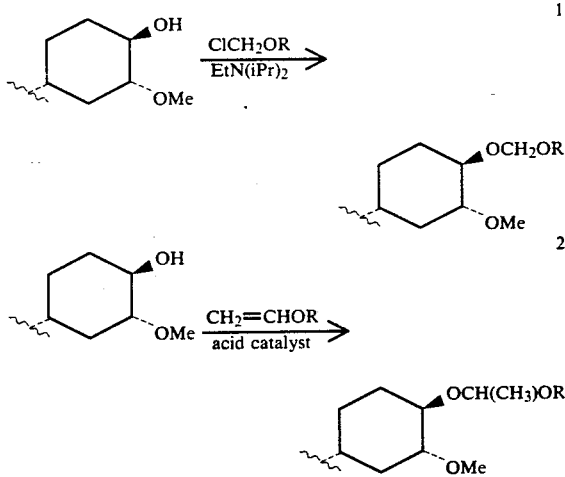

The various acetal-forming agents include chloromethlylmethyl ether, chromomethylmethyl sulfide, benzyl chloromethyl ether, t-butyl chloromethyl ether, 2-methoxyethoxymethyl chloride, 2,2,2-trichloroethoxymethyl chloride, bis(2-chloroethoxy)methyl chloride, 2-(trimethylsilyl)ethoxymethyl chloride, 2,3-dihydropyran, 2,3-dihydrothiopyran, 4-methoxy-2,3-dihydropyran, 4-methoxy-2,3-dihydrothiopyran-S, S-dioxide, tetrahydrofuran (and thionyl chloride), 2,3-dihydrofuran, ethyl vinyl ether, 2-methoxy-1-propene and isopropyl vinyl ether.

The following experimental procedures are included for illustrative purposes.

EXAMPLE 1

31-[O-(1-Methoxy-1-methyl)ethyl]rapamycin

To a solution of 5.0 g (5.47 mmol) of rapamycin in 5 mL of dry dichloromethane is added 1.05 mL (10.96 mmol) of 2-methoxy-1-propene followed by a catalytic amount of pyridinium p-toluenesulfonate and allowed to stir at room temperature for 4 h. The reaction was worked up by pouring into water and allowing to stir for 20 min at which time, the organic layer was separated, washed with brine, dried over sodium sulfate, filtered, and concentrated in vacuo to give a pale yellow foamy solid. The residue was purified via preparative HPLC chromatography (Rainin HPXL pumps, 2 diameter Dynamax silica column, 60% ethyl acetate/hexane, 35 mL/min), collecting 1.43 g (27%) of 31-[O-(1-methoxy-1-methyl)ethyl]rapamycin as a later eluting peak. The spectral data follow: $^1$H NMR (CDCl$_3$, 400 MHz) $\delta$4.82 (s, 1 H, anomeric OH), 3.41 (s, 3 H, —OCH$_3$), 3.28 (s, 3 H, —OCH$_3$), 3.15 (s, 3 H,—OCH$_3$), 3.10 (s, 3 H, —C(CH$_3$)$_2$CH$_3$), 1.81 (s, 3 H, CH$_3$C=C—), 1.67 (s, 3 H, CH$_3$C=C—); IR (KBr) 3430 (OH), 2920, 2860, 1725 (C=O), 1645 (C=O), 1450, 1375, 1190, 1090, 985 cm$^{-1}$; MS (neg.ion FAB) 985 (M—, 100), 167.

Analysis: Calc'd for C$_{55}$H$_{87}$NO$_{14}$.4 H$_2$O: C 62.41; H 9.05; N 1.32; Found: C 62.15; H 8.39; N 1.35.

EXAMPLE 2

42-[O-(1-Methoxy-1-methy]rapamycin

Using the above procedure, 120 mg (2.3%) of another compound, 42-[O-(1-methoxy-1-methyl)ethyl]rapamycin was isolated as a less polar fraction. The spectral data follow: $^1$H NMR (CDCl$_3$, 400 MHz) $\delta$4.82 (s, 1 H, anomeric OH), 3.34 (s, 3 H, —OCH$_3$), 3.28 (s, 3 H, —OCH$_3$), 3.14 (s, 3 H, —C(CH$_3$)$_2$OCH$_3$), 3.10 (s, 3 H, -OCH$_3$), 1.81 (s, 3 H, CH$_3$C=C—), 1.65 (s, 3 H, CH$_3$C=C—); IR (KBr) 3440 (OH), 2930, 2860, 1720 (C=O), 1645 (C=O), 1450, 1375, 1190, 1090, 985 cm$^{-1}$; MS (neg. ion FAB) 985 (M—, 100 ), 590, 446 (100), 175, 167.

Analysis: Calc'd for C$_{55}$H$_{87}$NO$_{14}$.1H$_2$O; C 65.77; H 8.93; N 1.40; Found: C 65.37; H 8.44; N 1.08.

EXAMPLE 3

31-[O-[2-(trimethylsilyl)ethoxy]methyl]rapamycin

To a stirred solution of 914 mg (1 mmol) of rapamycin in 5 ml of methylene chloride under an atmosphere of nitrogen was added 333 mg (1.5 mmol, 26.5 $\mu$l) of 2-(trimethylsilyl)ethoxymethyl chloride followed by dropwise addition of 258 mg (2.0 mmol, 348 $\mu$l) of ethyl diisopropylamine. After 30 minutes, the analysis (silica gel, eluted with ether) indicated the reaction was complete.

The reaction mixture was diluted with ethyl acetate and 0.1 N aqueous hydrochloric acid. The mixture was extracted twice with ethyl acetate and the combined extract washed successively with 0.1 N hydrochloric acid solution and aqueous sodium bicarbonate. The ethyl acetate solution was dried (magnesium sulfate) and concentrated to obtain the title compound, mp 80°-84° C. Tlc showed 1 spot.

Analysis: Calc'd for C$_{57}$H$_{93}$NO$_{14}$S; C, 65.99; H, 8.97; N, 1.24; Found: C, 65.49; H, 8.98; N, 1.34.

Immunosuppressive activity was evaluated in an in vitro standard pharmacological test procedure to measure lymphocyte proliferation (LAF) and in an in vivo procedure in which the survival time of a pinch skin graft was evaluated.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio, or as the percent inhibition of lymphoproliferation of 1 $\mu$M.

$$\frac{^3H\text{-control thymus cells} - H^3\text{-rapamycin-treated thymus cells}}{^3H\text{-control thymus cells} - H^3\text{-test compound-treated cells}}$$

The in vivo test procedure is designed to determine the survival time of pinch skin grafts from male DBA/2 donors transplanted to male BALB/c recipients. The method is adapted from Billingham R. E. and Medawar P. B., J. Exp. Biol. 28.385-402, (1951). Briefly, a pinch ski graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days ±S.D.) of the drug treatment group is compared with the control group.

The following table summarizes the result obtained with the compounds of Examples 1 and 2 in the three standard test procedures.

| Compound | LAF[1] | Skin Graft[2] |
|---|---|---|
| Rapamycin | 3.3–5.8 | 12.5 |
| Example 1 | 3.2 | 10.7 |
| Example 2 | 8.3 | — |
| Example 3 | 17.2 | — |

[1]IC$_{50}$ (nM)
[2]Mean survival days

Antifungal activity of the compounds of this invention was measured against 5 strains of *Candida albicans* using a plate test procedure for measurement of inhibition. The following represents the typical procedure used. Compound to be tested was placed on sterile dried ¼" plate disks, and allowed to dry. Agar plates were seeded with fungi and allowed to solidify. The impregnated disks were placed on the seeded Agar surface and incubated for the time required for the particular culture. Results are expressed in MIC ($\mu$g/ml) to inhibit growth. The results of this test procedure showed that the compounds of this invention have antifungal activity.

| | Anti-Candida Activity ($\mu$g/mL)* | | | | |
|---|---|---|---|---|---|
| Compound | ATCC 10231 | ATCC 38246 | ATCC 38247 | ATCC 38248 | 3669 |
| Rapamycin | 0.03 | 0.25 | 0.03 | 0.006 | 0.25 |
| Example 1 | 0.025 | 0.4 | 0.025 | 0.10 | 0.4 |
| Example 2 | 0.025 | 0.4 | 0.025 | 0.1 | 0.2 |

*Minimal Inhibitory Concentration (MIC)

Based on the results of these standard pharmacological test procedures, the compounds are useful in the treatment of transplantation rejection such as, heart, kidney, liver, bone marrow, and skin transplants; automimmune diseases such as, lupus, rheumatoid arthritis, diabetes mellitus, myasthenia gravis, and multiple sclerosis; and diseases of inflammation such as psoriasis, dermatitis, eczema, seborrhea, inflammatory bowel disease; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredients. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administrated intravenously. The compound can also be administered orally either in liquid or solid composition form.

What is claimed is:

1. A compound according to the formula:

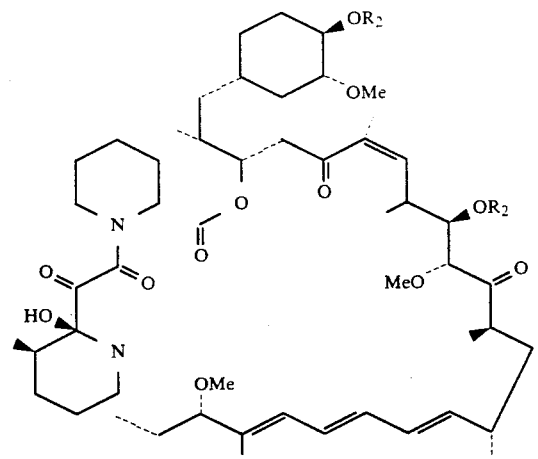

wherein $R^1$ and $R^2$ independently are hydrogen, $-CH_2YX$, $-C(CH_3)_2YX$, $-CH_2(CH_3)YX$, or L; Y is O or S; X is $-CH_3$, $-(CH_2)_nCH_3$, , $-CH_2C_6H_6$, $-(CH_2)_2OCH_3$, $-CH_2Cl_3$ or $-CH_2CH_2Si(CH_3)_3$ and L is selected from tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-S, S-dioxide-2-yl with a provision that $R^1$ and $R^2$ cannot simultaneously be hydrogen and n is 1–5.

2. A compound according to claim 1 which is 31-[O-(1-methoxy-1-methyl)ethyl]rapamycin.

3. A compound according to claim 1 which is 42-[O-(1-methoxy-1-methyl)ethyl]rapamycin.

4. A compound according to claim 1 which is 31-[O-[2-trimethylsilyl)-ethoxy]methyl]rapamycin.

5. A method of treating transplant rejection and host vs graft disease, autoimmunine disease and disease of inflammation in a mammal by administering thereto an effective amount of a compound having the formula:

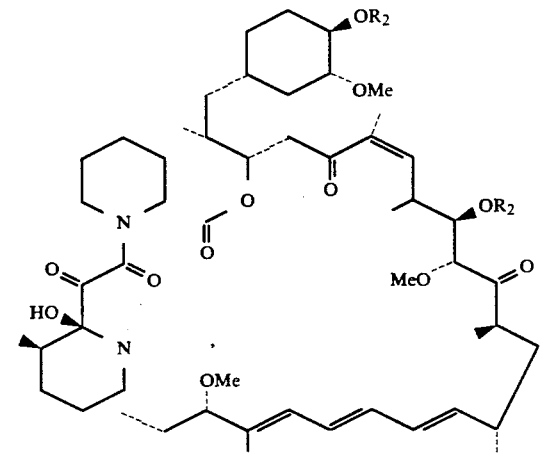

wherein $R^1$ and $R^2$ independently are hydrogen, $-CH_2YX$, $-C(CH_3)_2YX$, $-CH_2(CH_3)YX$, or L; Y is O or S; X is $-CH_3$, $-(CH_2)_nCH_3$, $-CH_2C_6H_6$, $-(CH_2)_2OCH_3$, $-CH_2Cl_3$ or $-CH_2CH_3Si(CH_3)_3$ and L is selected from tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran- 2-yl, or 4-methoxytetrahydrothiopyran-S, S-dioxide-2-yl with a proviso that R¹ and R² cannot simultaneously be hydrogen and n is 1-5.

6. A method according to claim 5 wherein the compound used is 31-[O-(1-methyl)ethyl]rapamycin.

7. A method according to claim 5 wherein the compound used is 42-[O-(1-methoxy-1-methoxy)ethyl]rapamycin.

8. A method according to claim 5 wherein the compound used is 31-[O-[2-(trimethylsilyl)ethoxy]methyl]-rapamycin.

9. A method of treating fugal infections in mammals by administering thereto an effective amount of a compound having the formula:

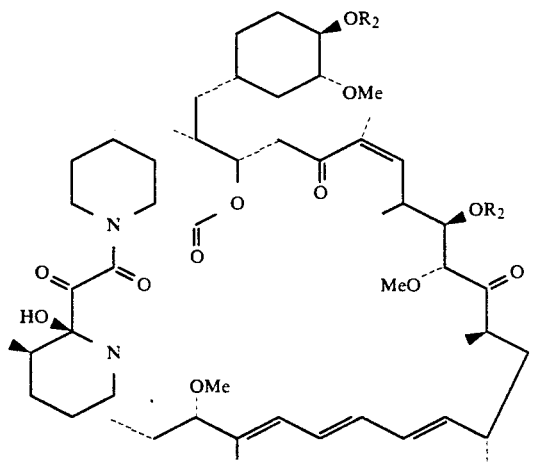

wherein R¹ and R² independently are hydrogen, —CH₂YX, —C(CH₃)₂YX, —CH₂(CH₃)YX, or L; Y is O or S; X is —CH₃, —(CH₂)$_n$CH₃, —CH₂C₆H₆, —(CH₂)₂OCH₃, —CH₂Cl₃ or —CH₂CH₂Si(CH₃)₃ and L is selected from tetrahydrofuran-2-yl, tetrahydrothiophen-2-yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-S, S-dioxide-2-yl with a provision that R¹ and R² cannot simultaneously be hydrogen and n is 1-5.

10. A method according to claim 9 wherein the compounds used is 31-[O-(1-methyl)ethyl]rapamycin.

11. A method according to claim 9 wherein the compound used is 42-[O-(1-methoxy-1-methyl)ethyl]rapamycin.

12. A method according to claim 9 wherein the compound used is 31-O-[2-(trimethylsilyl)ethoxy]methyl]-rapamycin.

13. A pharmaceutical composition comprising
(a) an effective amount of a compound according to the formula:

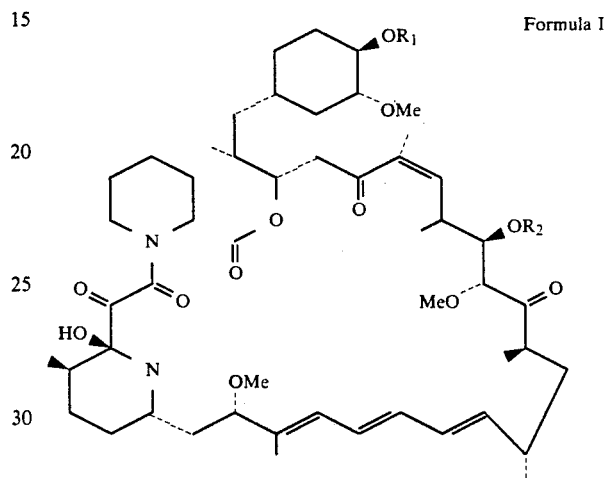

Formula I wherein R¹ and R² independently are hydrogen, —CH₂YX, —C(CH₃)₂YX, —CH₂(CH₃)YX, or L; Y is O or S; X is —CH₃, —(CH₂)$_n$CH₃, —CH₂C₆H₆, —(CH₂)₂OCH₃, —CH₂Cl₃ or —CH₂CH₂Si(CH₃)₃ and L is selected from tetrahydrofuran-2-yl, tetrahydrothiophen-2yl, tetrahydrothiopyran-2-yl, tetrahydropyran-2-yl, 4-methoxytetrahydropyran-2-yl, 4-methoxytetrahydrothiopyran-2-yl, or 4-methoxytetrahydrothiopyran-S, S-dioxide-2-yl with a proviso that R¹ and R² cannot simultaneously be hydrogen and n is 1-5, and
(b) a pharmaceutical carrier.

* * * * *

UNITED STATES PATENT AND TRADEMARK OFFICE
CERTIFICATE OF CORRECTION

PATENT NO. : 5,151,413
DATED : September 29, 1992
INVENTOR(S) : Craig Caufield et al It is certified that error appears in the above-indentified patent and that said Letters Patent is hereby corrected as shown below:

At column 1, lines 45-64, column 6, lines 1-20, column 6, lines 43-63, column 7, lines 18-36, column 8, lines 15-33, and in the abstract, the formula shown should be

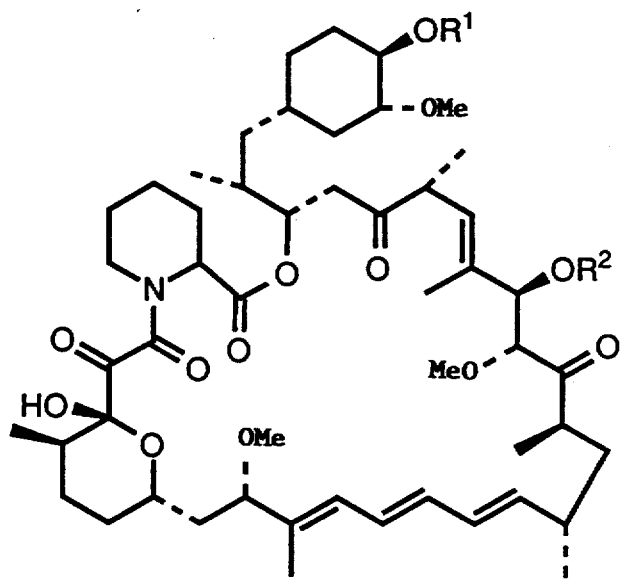

Signed and Sealed this

Sixth Day of December, 1994

Attest:

BRUCE LEHMAN

Attesting Officer    Commissioner of Patents and Trademarks